United States Patent [19]

Sparer et al.

[11] Patent Number: 4,513,034

[45] Date of Patent: Apr. 23, 1985

[54] VARIABLE PERMEABILITY LIQUID CRYSTALLINE MEMBRANES

[75] Inventors: Randall V. Sparer; Ravi K. Bhaskar, both of Lawrence, Kans.

[73] Assignee: Merck & Co., Inc., Rahway, N.J.

[21] Appl. No.: 620,409

[22] Filed: Jun. 14, 1984

[51] Int. Cl.³ .............................. C09K 3/34; G02F 1/13
[52] U.S. Cl. .......................................................... 428/1
[58] Field of Search ............................................ 428/1

[56] References Cited

U.S. PATENT DOCUMENTS

| | | | |
|---|---|---|---|
| 3,871,904 | 3/1975 | Haas et al. | 428/1 |
| 3,977,767 | 8/1976 | Okuma et al. | 428/1 |

Primary Examiner—William J. Van Balen
Attorney, Agent, or Firm—Mario A. Monaco; Michael C. Sudol, Jr.; R. Brent Olson

[57] ABSTRACT

The instant invention is directed to a variable permeability liquid crystalline membrane, comprising a porous structure containing a polymeric liquid crystal which can undergo a phase change.

The instant invention is also directed to a process for regulating the flow of solutes or permeants through a liquid crystalline membrane, comprising changing the phase of a polymeric liquid crystal supported by a porous structure.

9 Claims, 3 Drawing Figures

VARIABLE PERMEABILITY LIQUID CRYSTALLINE MEMBRANES

BACKGROUND OF THE INVENTION

This invention relates to liquid crystalline membranes.

Modern techniques of controlled drug release date back to 1964 and began with the discovery that organic molecules could diffuse through silicone rubber membranes.

Almost all controlled release systems described have a common feature: the rate of release of the drug (hereafter referred to as the "permeant") is either constant, as in the case of reservoir type devices, or decreases with time according to some known profile, as in the case of matrix type devices.

Drug delivery devices may be broadly classified into two groups—the passive reservoir and matrix type devices in which the drug diffuses through or across some kind of rate limiting barrier (hereafter referred to as a membrane) or the "active" kinds of devices such as the osmotic pumps which rely on osmotic pressure differentials to deliver drugs. Mechanical and electromechanical drug delivery systems (U.S. Pat. Nos. 3,911,911 and 3,777,748) have tended to be relatively more complex than their passive counterparts. It is evident that delivery systems of the future will be required to incorporate the pharmacological flexibility of the active delivery systems without the associated considerations of increased cost and complexity. These requirements reduce to the need for a non-mechanical valve; i.e., a variable permeability membrane.

The central feature of the problem is the permeability of the membrane system involved, and the means to trigger or regulate it by means of some external agency without serious damage to the living tissues in which the device is implanted.

Several methods to control the permeability of membranes immersed in aqueous media have been reported in the literature. Briefly, the permeability of a membrane system may be enhanced by two classes of methods: modification of membrane structure and modification of the membrane's surrounding environment.

Permeability may be controlled by means of modification of a membrane's environment relating to boundary layer effects, i.e. the "unstirred" film immediately adjacent to the membrane surface (Lakshminarayanaiah, N.; "Transport phenomena in Membranes," Academic Press, New York, N.Y.; (1969), p. 129.). Among the factors examined were the relative abundance of protons in the boundary layer (Lobel, F.; and Caplan, S. R.; Journal of Membrane Science, 6, 1980, 221-234.) thickness of the boundary layer, temperature, etc. Some authors (Pasechnik, V. A.; and Cherkasov, S.; Kolloidnyi Zhurnal, 42 (4), (1980), 748-751.) have reported an increase in the permeability of ultrafiltration membranes caused by a breakdown of water in the boundary layers, which in turn was caused by an applied electric field.

Examples of triggering by modification of membrane structure have been rather more numerous—specifically, photochemical, magnetic (Langer, R.; Proc. Natl. Acad, Sci. U.S.A., (1981), 3, 1863-1867.), thermal (Rogers, C. E.; "Controlled Release Polymeric Formulations," Plenum Press, New York, N.Y., pg. 15-25), and electrical (Grodzinsky, A. J. and Eisenberg, S. R.; Proceedings of the International Conference of Biomedical Engineering, 1980.) have been reported. Of these, only magnetic triggers have been demonstrated as potentially useful for controlled release applications.

A BRIEF DESCRIPTION OF THE DRAWINGS

DESCRIPTION OF THE INVENTION

Figure 1:
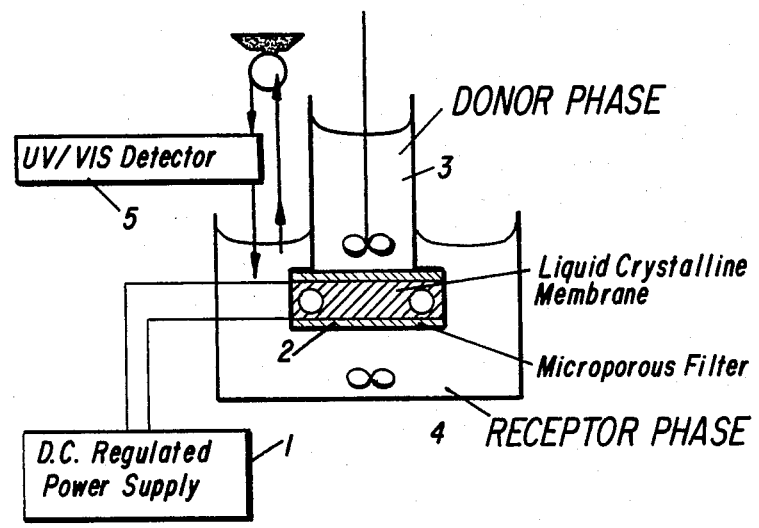
FIG. 1 is a diffusion cell containing the liquid crystalline membrane.

The instant invention is directed to a variable permeability liquid crystalline membrane, comprising a porous structure containing a polymeric liquid crystal which can undergo a phase change.

The only constraint on the formation of the porous structure is that it should permit access to the liquid crystal by the triggering agent; for example, structures used with electrical triggers should allow for a quasi-continuous liquid crystalline layer between the electrodes; structures used with thermal and magnetic triggers should have a high thermal conductivity and/or magnetic susceptibility.

The instant invention is also directed to a process for regulating the diffusion of permeants through a liquid crystalline membrane, comprising changing the phase of a polymeric liquid crystal supported by a porous structure.

Any porous structure may be used. Examples include any water insoluble porous membrane which maintains its physical integrity in the presence of the solvent, if any. The purpose of the porous structure is to maintain the liquid crystal in a membrane configuration. If applied voltage is used, the porous structure must allow electric current to pass through the electric current phase (i.e. connected pore structure). Examples of porous structures include amorphous polymers, such as polycarbonates; cellulose esters as microporous matrices or sheets; solvent resistant polymers that may be formed into "honeycomb"-like matrices, such as phenolic polymers, polysulfone, polyphenylene sulfide and the like. The preferred polymeric porous #substrate are cellulose acetate esters.

Any external agency which causes a phase change in the polymeric liquid crystal may be used. Examples include applied voltage, temperature change, magnetic fields, and the like. Electrical triggering may be accomplished by applying an electric field perpendicular to the membrane surface by means of porous electrodes. Magnetic fields may be applied by locating the membrane system between the poles of a magnet or by winding a magnetic-field inducing solenoid around the membrane. Thermal transitions may be triggered by raising the temperature of the sample through electrical, convective or dielectric heating. The last mentioned is extremely effective in bringing about a rapid response and is accomplished by applying a low voltage high frequency alternating current field across the membrane.

Any polymeric liquid crystal which can undergo a phase change may be used. Examples include polypeptides, such as poly-γ-benzyl-L-glutamate, preferably having a molecular weight range of 20,000 to 300,000 as determined by light scattering; poly(alkoxy phosphazenes), preferably having a molecular weight range of 50,000 to 200,000 as determined by gel permeation chromatography; block copolymers of lyophilic and hydrophilic components, such as polystyrene/poly(ethylene oxide), polybutadiene/poly(carbobenzoxy-L-lysine), preferably having a molecular weight of 30,000 to 80,000; poly(amide-hydrazides), preferably having a molecular weight of 50,000 to 150,000 as determined by gel permeation chromatography; and mesogenic substituted polymethacrylates.

The polypeptide liquid crystalline membranes will undergo a phase change by electrical, magnetic and thermal means. The poly(alkoxy phasphazenes) will undergo a phase change by thermal means. The block copolymers will undergo a phase change by lyotropic and thermal means. The poly(amide-hydrazides) will undergo a phase change by thermal and electrical means. The mesogenic substituted polymethacrylates will undergo a phase change by electrical and magnetic means.

The polymer is preferably mixed with a solvent. Any solvent may be used in which the polymer is soluble and when dissolved the resulting solution is not miscible in water. Examples include halogenated methanes, such as dichloromethane; chloroform, carbon tetrachloride, acetonitrile, cyclohexane, tetrachloroethane, dimethylsulfide, toluene, tetralin, m-exylene, styrene, nonane and hexane. In general, any non-polar solvent for which $S(H) \geq 8.0$. If the polymer is a polypeptide, any $\alpha$-helicogenic solvent may be used.

If the polymer is mixed with a solvent, it is preferred to allow sufficient time for the polymer solution to become liquid crystalline, usually 12 hours is sufficient. The required time may be determined by a variety of techniques, such as melting point, refractive index, viscosity or numerous other measurable physical changes.

The liquid crystal may be sandwiched between structure, or otherwise saturating the porous structure. The only critical element is that the porous structure spatially contain the liquid crystal.

The amount of polymeric crystal is variable. The polymeric concentration must be such that external stimulus can trigger the phase change. For poly-$\gamma$-benzyl-L-glutamate, it is preferred to use at least 15%, weight/volume, most preferably 15 to 23%, weight/volume, based on the combined weight of the crystal and solvent. For most polymeric liquid crystals the preferred percent weight/volume is 10 to 30% w/v.

In one embodiment, the solution, when freshly made, is in the isotropic phase but slowly converts to the cholesteric phase when allowed to stand. The cholesteric phase is the most stable phase at room temperature from a thermodynamic viewpoint. When subject to an electric field of strength 300–500 volts per centimeter, the cholesteric phase undergoes a rapid and reversible transition to the nematic phase at room temperature. The nematic phase of the liquid crystal posseses an order that is substantially different from the ordering of the cholesteric phase; and this difference is used to advantage in this invention. Any means of triggering the cholesteric to nematic transition known to those skilled in the art may be used with this invention.

EXAMPLES

Construction of the Membrane

The membrane used in the example was composed of a 23% w/v solution of poly($\gamma$-benzyl-L-glutamate) in dichloromethane, confined to a thickness of 1 mm by the use of two cellulose acetate microporous sheets between which it was sandwiched.

The inner surfaces of two 25 mm diameter microporous filters made from cellulose acetate (Amicon C-300) were coated with a layer of gold/palladium 400 Angstroms in thickness to render them electrically conductive. The pores of the filters were not blocked during the coating procedure. A silicone rubber "O" ring was placed as a spacer between the filters and provided a cavity which was filled with the liquid crystal, as shown in FIG. 1. Fine wires connected to the inner surfaces of the filters facilitated the application of an electric field across the liquid crystal. The entire assembly was sealed with silicone rubber cement to preclude the formation of leaks. When an electric field was applied to the membrane, the liquid crystal underwent a transition from the cholesteric to the nematic phase and the permeability of the membrane to any permeant that is soluble in water increased. When the field was switched off the membrane it reverted to the cholesteric phase after a time lag of 4–5 hours. The membrane thus functioned as a "gate" to control the permeability of the solute.

The time lag for the reversion of the nematic phase to the cholesteric phase is of viscous origin. This time lag may be reduced by decreasing the molecular weight of the polymer dissolved in the dichloromethane. However, doing so also decreases the cholesteric pitch of the liquid crystalline molecules and increases the value of the minimum field strength required for the transition; thus the advantages of lower reversion time may be offset by the larger values of the electric field required to trigger the membrane.

EXAMPLE I

Figure 2:
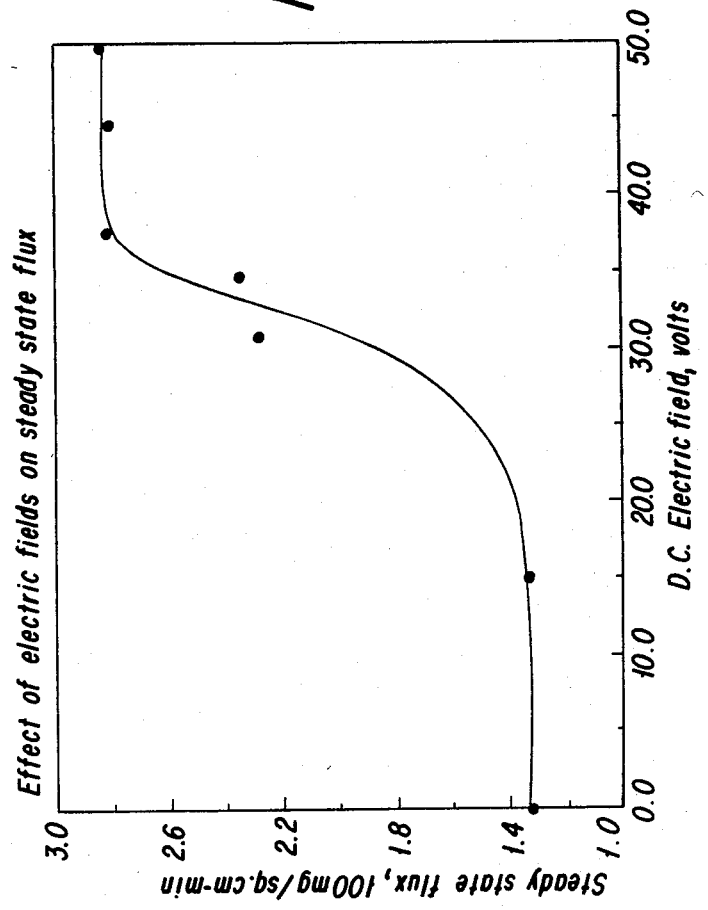
FIG. 2 is a graph of the effect of electric fields on steady state flux in Example 1.

The membrane was clamped in a modified Amicon model 8010 ultrafiltration cell. Ten milliters of a solution containing 0.0998 milligrams per milliter of the dye methylene blue were introduced into the upper compartment (hereafter referred to as the "donor phase"). The lower compartment (hereafter referred to as "the receptor phase") was filled with 1000 milliters of distilled water buffered at a pH of 7.0. Both compartments were stirred continuously, and the concentration of dye in the receptor phase was monitored by pumping it through an ultra-violet detection apparatus mounted in a Varian Associates Cary 219 spectrophotometer. The procedure was repeated with an electric field applied to the membrane. Diffusional lag times for the permeation of the dye through the membrane were found to decrease when the field was applied. Steady-state fluxes of the dye were found to increase from 70% to 112% over baseline values when the electric field strengths were increased from 0.0 to 500 volts per centimeter, as shown in FIG. 2.

FIG. 1 shows the configuration of the membrane system. The leads from the D.C. regulated power supply (1) are connected to the inner surfaces of the filters (2). The cell body itself serves as the donor compartment (3). The solution in the receptor compartment (4) was pumped continuously through the UV-VIS detector (5).

EXAMPLE II

The membrane was prepared as described above, and subjected to a 7.5 hour diffusion run. The electric field was turned off after 3.5 hours, when it was observed that the enhanced steady-state flux was maintained even after the field was discontinued. This revealed that the enhancement of permeability was caused by a liquid crystalline transition and not by electro-osmotic or related effects.

EXAMPLE III

Figure 3:
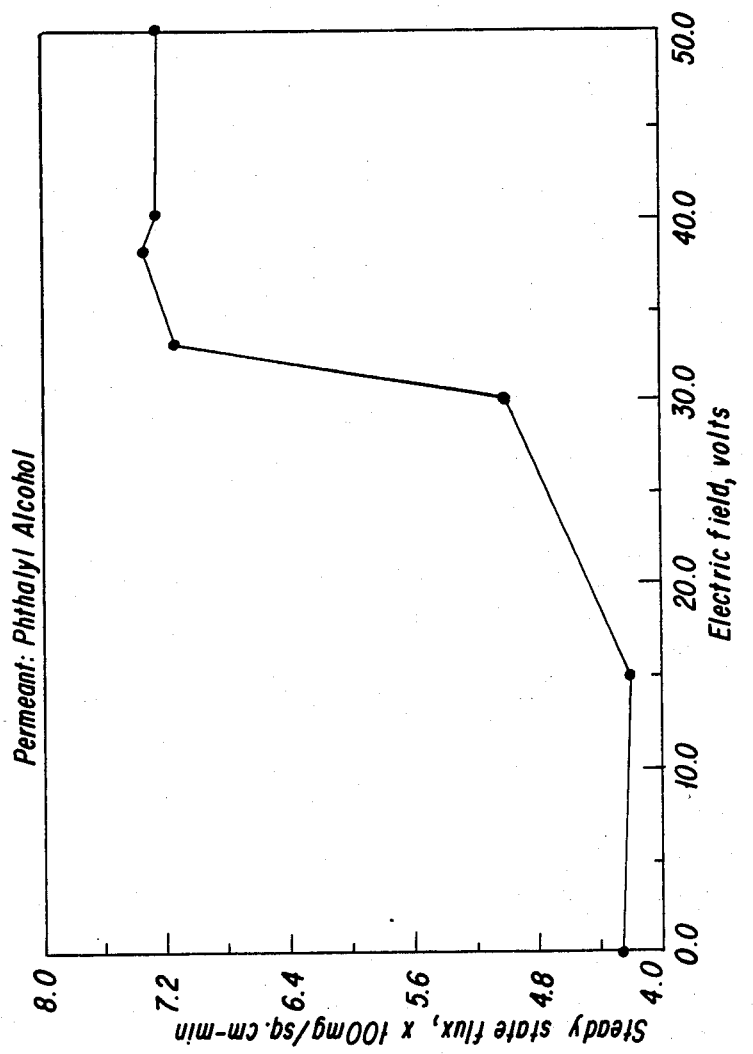
FIG. 3 is a graph of the effect of electric fields on steady state flux in Example 3.

The membrane was prepared as described above, and benzene 1,2 dimethanol (phthalyl alcohol) was used as the permeant. Although the lag times and steady state fluxes were not precisely the same as for methylene blue, the data showed the increase in steady state flux to be the same as for the anionic dye, 70–110%, as shown in FIG. 3.

EXAMPLE IV

Poly-γ-benzyl-L-glutamate of molecular weight 30,000 was used to prepare the membrane. The electric field strength required to trigger the membrane was twice the value (780 volts per centimeter) as that required for a polymer with a molecular weight of 310,000. This was additional evidence that the increase in permeability was due to the electrotropic cholesteric to nematic phase transition of poly-γ-benzyl-L-glutamate that comprised the liquid crystalline membrane.

What is claimed is:

1. A variable permeability liquid crystalline membrane, comprising a porous structure containing a polymeric liquid crystal which can undergo a phase change.
2. The membrane of claim 1, wherein said porous substrate is a cellulose ester microporous membrane.
3. The membrane of claim 2, wherein said liquid crystal is poly-γ-benzyl-L-glutamate.
4. The membrane of claim 3, wherein 15 to 23%, by weight, of poly-γ-benzyl-L-glutamate and 77 to 85%, by weight, of solvent is used.
5. A process for regulating the diffusion of solutes or permeants through a liquid crystalline membrane, comprising changing the phase of a polymeric liquid crystal supported by a porous structure.
6. The process of claim 5, wherein the phase of said polymeric liquid crystal is changed by subjecting said crystal to an electric field of 300 to 500 volts per centimeter.
7. The process of claim 5, wherein said porous substrate is a cellulose ester microporous filter.
8. The process of claim 7, wherein said cellulose ester is poly-γ-benzyl-L-glutamate.
9. The process of claim 8, wherein 15 to 23%, by weight, of poly-γ-benzyl-L-glutamate and 77 to 85%, by weight, of solvent is used.

* * * * *